United States Patent [19]

Schmitz

[11] Patent Number: 4,637,931
[45] Date of Patent: Jan. 20, 1987

[54] POLYACTIC-POLYGLYCOLIC ACID COPOLYMER COMBINED WITH DECALCIFIED FREEZE-DRIED BONE FOR USE AS A BONE REPAIR MATERIAL

[75] Inventor: John P. Schmitz, Columbia, Md.

[73] Assignee: The United States of America as represented by the Secretary of the Army, Washington, D.C.

[21] Appl. No.: 658,945

[22] Filed: Oct. 9, 1984

[51] Int. Cl.$^4$ ..................... A61K 31/74; A61K 35/32
[52] U.S. Cl. ........................................... 424/78; 424/95
[58] Field of Search ..................................... 424/95, 78

[56] References Cited

U.S. PATENT DOCUMENTS

| | | | |
|---|---|---|---|
| 4,172,128 | 10/1979 | Thiele et al. | 424/95 |
| 4,440,750 | 4/1984 | Glowacki et al. | 424/95 |
| 4,526,909 | 7/1985 | Urist | 424/95 |

Primary Examiner—Sam Rosen
Attorney, Agent, or Firm—John H. Raubitschek; Arthur I. Spechler; Werten F. W. Bellamy

[57] ABSTRACT

A novel bone repair material consisting essential of decalcified freeze-dried bone and biodegradable, biocompatible copolymer has been developed for improving and accelerating the healing of osseous tissue. The bone repair material was prepared by combining decalcified bone with a copolymer consisting essentially of a 50:50 poly(L)(−)lactide co-glycolide.

19 Claims, No Drawings

POLYACTIC-POLYGLYCOLIC ACID COPOLYMER COMBINED WITH DECALCIFIED FREEZE-DRIED BONE FOR USE AS A BONE REPAIR MATERIAL

BACKGROUND OF THE INVENTION

One of the most challenging tasks facing those in the fields of dentistry and orthopedic medicine has been the architectural reconstruction of osseous defects which may have been a sequela of infection induced bony/sequestration, developmental malformation, surgical resection, or traumatic avulsion. The need to initiate repair and to restore structurally deficient bone has prompted the development and application of a wide assortment of materials.

The biodegradable synthetic polymers, specifically, copolymers of polylactic (PLA) and polyglycolic acid (PGA), appear to satisfy many of the requirements necessary to replace autogenous cancellous marrow as the grafting material of choice for maxillofacial defects. This material has the advantages of being otainable in large amounts and possessing a long shelf-life. Additionally, the use of this material (1) eliminates the need for a second surgical procedure in the host; (2) elicits minimal tissue reaction; (3) predictably biodegrades without forming toxic metabolites; (4) has the ability to act as a trestle for bony ingrowth; and (5) and may also possess osteogenic potential. Applicant has discovered that a combination of polylactic and polyglycolic acid copolymers and decalcified freeze-dried bone are able to produce a synergistic response with respect to osseous healing. This results in the accelerated osseous regeneration and a subsequent reduction in the amount of morbidity associated with maxillofacial avulsive injuries.

Maxillofacial injuries sustained in a combat environment account for a significant portion of combat-related injuries. It has been reported by Tinder et al. in "Maxillofacial Injuries sustained in the Vietnam Conflict", *Military Medicine*, Vol. 134, pages 668-672, 1969 that:

(1) During the Vietnam conflict for the year ending June 30, 1968, approximately 8.6–11.1% of U.S. Army patients admitted for trauma sustained injuries to the maxillofacial region;

(2) In patients whose injuries involved concomitant facial bone fractures, the mandible was the most frequently fractured bone; and (3) In patients with mandibular injuries, 54% sustained avulsions of a significant portion of the mandible.

In the U.S. Navy Maxillofacial Casualty Study of patients with maxillofacial injury, reported by in 1980 by J. E. Kelly in *Management of War Injuries to the Jaws and Related Structures*, bone grafts for cases of avulsive osseous injury were required approximately 45% of the time. The mandible was again found to be the most frequently fractured facial bone with 86% of mandibular grafts being performed unilaterally.

In view of the findings that large percentage of maxillofacial injuries were unilateral mandibular avulsive wounds, much of the effort in maxillofacial graft or implant research has been directed towards using the mandible as the prototype to asess maxillofacial healing.

There is unanimity of opinion at the present time that for grafting large mandibular defects, autogenous bone is the preferred grafting material with the ileum the most desirable donor site. Complications involved with iliac crest donor procedures include an estimated blood loss of from 200–400 cc along with infrequent occurrences of adynamic ileus and herniation. Although the ileum provides a suitable supply of hematopoietic cancellous marrow, there are instances when contour and adaptability are better obtained through the use of rib grafts (i.e. restoration of the curvature of the mandibular symphysis). Harvesting of ribs is additionally associated with a 25–35% incidence of pneumothorax.

While small defects of 1 cm or less may be corrected by the use of sliding bone grafts, larger discontinuity grafts may require the use of metal trays to contain the graft. Perforation of the tray through mucosa may require a second surgical procedure for removal or to control infection. In addition, in long span cases, there is a tendency for inadequate osseous proliferation especially in the middle of the graft. The above morbidity translates into an 84% success rate for grafting mandibular discontinuity defects with autografts.

In light of the preceeding discussion concerning methods of mandibular grafting, alternative methods have been sought in the form of alloimplants and allografts. The morbidity associated with autograft procedures makes the search for an alloimplant or allograft even more prudent. The biodegradable synthetic polymers have been investigated as osseous alloimplants due to the following characteristics:

(1) adequate initial strength;
(2) controlled rate of degradation;
(3) complete absorbability without the formation of toxic metabolites (hydrolytic byproducts are processed through the tricarboxylic acid cycle and eliminated as carbon dioxide via respiration); and
(4) minimal inflammatory response from the host.

Many of these polymers, however, are severely lacking either in their initial strength or their rate of degradation. Only the polyesters polydioxanone (PDS), polyglycolic acid (PGA), and polylactic acid (PLA) possess adequate strength and a predictable degradation rate. Of these, copolymers of PGA and PLA have demonstrated an accelerated rate of osseous wound healing. Homopolymers of PLA and PGA and copolymers of PGA/PLA have been investigated for use as absorbable sutures, as implants to repair fractures of the orbital floor, as biodegradable plates for internal fixation of mandibular fractures, and as foam meshworks to facilitate healing extraction sockets. Both homopolymers of PGA and PLA as well as copolymers of PGA/PLA, produce only a minimal to slight inflammatory response in tissue. Degradation of PGA/PLA copolymers occurs by random hydrolytic cleavage of ester linkages in the chain and is independent of enzymatic activity. There is evidence that metabolites of copolymer degradation are processed through the Krebs cycle and eliminated as carbon dioxide through respiration. Copolymers of 25% PGA have been found to degrade fastest followed by 50% PLA:50% PGA, 75% PLA:24% PGA, and homopolymers of PLA and PGA, respectively. During the requisite period necessary for fracture fixation (4–10 weeks), 50PLA:50PGA will degrade roughly 50%, completing 100% dissolution in 120 days.

The mechanical properties of PGA/PLA copolymers have been found to vary depending on their percent composition and degree of crystallinity. DL-polylactide which is less crystalline than the L(−)-polylactide seems to be more susceptible to hydrolytic degradation. The DL-polylactide also has a problem with dimensional stability manifested as shrinkage following implantation.

From a morphological standpoint, the irregular, open-lattice type of texture visible on SEM photomicrographs makes the copolymer an ideal trestle to promote bony ingrowth as well as a carrier for other osteoinductive agents.

SUMMARY OF THE INVENTION

This invention relates to a novel composition and method for improving and promoting the healing of osseous tissue which comprises implanting at the site of the broken osseous tissue a therapeutically-effective amount of a composition comprising decalcified freeze-dried bone incorporated into a biodegradable polymeric matrix. More precisely, applicant's invention is directed to a novel formulation comprising a decalcified freeze-dried bone, in the amount of 40 to 60 percent by weight, is incorporated into a copolymer of poly(L)(−)lactide co-glycolide polymeric matrix which is implanted at the site of the broken osseous tissue to improve and promote the healing of said tissue. Applicant has found that the preferred composition consists essentially of a copolymer of 50:50 poly(L)(−)lactide co-glycolide and the decalcified freeze-dried bone in an amount of about 45 to 55 percent, preferably 50 percent, by weight of the copolymer. The most preferred composition consists essentially of cortical bone with a particle size in the range of 149 to 590 μm, preferably 200 to 400 μm, which has been decalcified in 0.6 normal hydrochloric acid.

The use of allogeneic bone provides an excellent alternative to autogenous bone. In an attempt to reduce the antigenicity associated with allogeneic bone, freeze-drying has been employed with the greatest success. Freeze-dried cortical bone has been shown to elicit little or no humoral or cell-mediated response and is the least antigenic of other bone allografts.

Provided a proper freeze-drying cycle is employed and a vacuum seal maintained, freeze-drying can also provide an almost unlimited shelf life while retaining biodynamics. Clinical results using various freeze-dried bone preparations have yielded success rates approaching autogenous grafts (70–90%) with a negligible infection rate.

The comparable, yet varying success rates of freeze-dried and autogenous bone have been attributed to the bone-induction principle. This principle is mediated through an acid-insoluble protein complex (bone morphogenetic protein). Bone morphogenetic protein (BMP) directs the differentiation of pluripotential mesenchymal cells into osteoprogenitor cells which form osteoblasts. The ability of bone allografts to transfer this bone induction principle has been shown to be highest for freeze-dried cortical bone which has been decalcified in 0.6 N HCl. While the issue of the particle size does not appear to be completely resolved, it seems tenable that grafts with a particle size in the range of 200–400 μm have a much greater proportional surface area and, therefore, should be able to provide a more readily available source of BMP than particles with a size in the 1–2 mm range.

Sterilization is an additional problem when preparing bone for preservation and clinical use. Boiling, autoclaving, and irradiation over 2.0 mrads is sufficient to destroy or alter the BMP present in the bone matrix. Sterilization by chemical means (ethanol) or ethylene oxide is preferred.

EXAMPLE SECTION

The herein offered example provides a method for illustrating, without any implied limitation, the practice of this invention in the treatment of osseous wounds.

This profiled experiment has been chosen to illustrate the osseous tissue healing activity of the copolymer-decalcified freeze-dried bone composites. Applicant prefers to use a copolymer of poly(L)(−)lactide co-glycolide as the polymeric matrix.

All temperatures not otherwise indicated are in degrees Celsius (o) and parts or percentages are given by weight.

MATERIALS AND METHODS

A description of fabrication of this invention follows:
PREPARATION OF ALLOGENEIC DECALCIFIED FREEZE-DRIED BONE (DFDB)
I. Harvesting:
   A. Aseptically remove cortical bone from donor (tibia, humerus, femur, radius/ulna) immediately after death.
   B. Remove soft tissue (macroscopically); epiphysis and cartilaginous tissue removed with rongeurs.
   C. Marrow/hematopoeithic elements should be removed by rinsing in physiologic saline/deionized water.
   D. Cleansed cortical bone is immediately placed into liquid nitrogen (−195° C.); leave at least 25 min. to 3 hrs.
   E. Transfer to freezer (−78° C. to −80° C.); store for at least 48 hrs.
II. Pulverization:
   A. Cut into 1 cm segments.
   B. Grind in bone mill @4° C. (not greater than 20 sec. bursts).
   C. Sieve to 149 micrometers to 590 micrometers then return to freezer at −78° C. for 4 hrs.; record weight of ground bone.
III. Processing:
   A. Defat: 95% ethanol (10 cc/gm ground bone) at 25°–30° C. for 4 hrs. with magnetic stirring; decant supernatant; Rinse in sterile distilled water three times for five minutes each.
   B. Decalcify: 0.6 N HCl (10 cc/gm ground bone) at 4° C. for 24 hrs. with magnetic stirring; after 12 hrs.—decant supernatant and replace with a second aliquot of 0.6 N HCl (10 cc/gm ground bone).
   C. Rinse: volumes used for rinsing are equal to the volume of acid utilized for decalcification;
      (1) prepare 0.1 M phosphate buffer (pH 7.4):
         Na 2HP04.2H20......9.73 gm.
         Na H2P04.2H20......1.87 gm.
         q.s. to 1 liter distilled water; sterilize.
      (2) rinse sterile distilled water 4°–7° C. for 10 min. with magnetic stirring (10 cc/gm); decant supernatant.
      (3) rinse 0.1 M phosphate buffer (PBS) 4°–7° C. for 10 min. with magnetic stirring (10 cc/gm); decant supernatant.
      (4) repeat rinse with deionized water and PBS (25°–30° C.) for 5 min. with magnetic stirring; decant supernatant.
      (5) repeat rinse with deionized water and PBS (25°–30° C.) for 1–2 min. with manual stirring.
      (6) add volume of deionized water to bone and measure pH (greater than 6.9); repeat step No. 5 if necessary.

(7) transfer to ultra-low freezer (−78° C. to −80° C.); store for at least 48 hrs.

IV. Lyophilize:
   A. Turn on FTS lyophilizer 24 hrs. before use condenser −150° C. with vacuum) to lower tray temperature to −25° C.
   B. Insert specimens in lyophilizer and apply vacuum.
   C. After 24 hrs.—shut off all temperature and allow to return to room temperature under vacuum.
   D. Remove specimens in 7 days. Approximately 55–65 millitorr.
   E. Store in dessicator with Drierite® under house vacuum.

V. Preparation of implants:
   A. Solubilize 1 gm coplymer 50:50 PLA/PGA in 10 cc chloroform with magnetic stirring for 20–30 min.
   B. Precipitate with 10 cc methanol; dry on filter paper.
   C. Add 0.5 gm DFDB, knead in tray and pack into mold.

VI. Polymerization:
   A. Place mold into vacuum heater at 46° C. for 24 hrs. under 28 in. Hg.
   B. Remove implants from mold and return to vacuum oven for an additional 24 hrs.
   C. Trim implants and weigh; place into sterilizer bags and record weights.
   D. Place implants into wide-mouth specimen jars and stopper loosely.

VII. Sterilization:
   A. Sterilize with ethylene oxide 40°–49° C. for 6 hrs.
   B. Place jars into lyophilizer at 44° C. for 84 hrs. at 100–150 millitorr.
   C. Stopper under vacuum.

Alternatively in Step III-A, the bone may be defatted with chloroform: methanol (50:50) for 4 hrs. at 25° C. (10 cc/gm.).

EXAMPLE

A composite alloimplant was prepared by combining a biodegradable, biocompatible polyester copolymer (poly(L)(−)lactide, co-glycolide) with freeze-dried decalcified bone. Diaphyseal segments of long bones were aseptically recovered from donors (New Zealand white rabbits). Marrow was removed from the bones and bones were ground in a Tekmoor Analytical Mill to a 150–590 micrometer particle size. The particles were then decalcified in 0.6 N HCL. The decalcified particulates were freeze-dried and stored in a dessicator until needed. The copolymer was solubilized in methanol and particulate freeze-dried decalcified bone was added until a 50:50 weight:weight ratio was achieved. The resulting composite was placed in a Teflon mold which was put into a vacuum oven for curing. Following curing, the implants' dimensions were 15 mm×4.0 mm. Ethylene oxide was used to sterilize the composite alloimplant. All alloimplants were degassed and stored in aseptic, vacuum conditions.

Following appropriate anesthesis, experimental wounds (15 mm OD) were aseptically and atraumatically prepared in the calvaria of 20 New Zealand white rabbits. The composite alloimplants were trimmed for a snug, frictional fit into ten of the animals. The remaining ten rabbits did not receive an implant and were the controls. All experimental sites were closed with soft tissue and 000-Dexon sutures.

Ten animals were euthanitized at four and eight weeks. Approximately two millimeters of host contiguous bone surrounding the composite alloimplant or untreated control would were recovered and the sites were evaluated clinically, radiographically, and histomorphometrically. The five control specimens recovered at four and eight weeks did not display any osseous healing across the 15 mm calvaria wound. Only fibrous tissue elements were observed. The composite alloimplant treated wounds at four weeks were surrounded by clinically normal appearing tissue. No adverse host implant reaction was evident. Remnants of implant were observed clinically. Radiographically, a two to four millimeter osteosclerotic rim was present at the wound margins. Occasional radiopaque islands could be seen within the healing wound. At the eight-week level, two of the five calvaria defects treated with the composite alloimplant displayed clinical evidence of complete bony bridging. The remaining three animals had a small central island of connective tissue rimmed by newly formed bone. All host tissue at the implant site appeared clinically to be normal and no implant remnants were observed. Radiographic evaluation confirmed the clinical observation: two cases, complete osseous regeneration was evident; three cases, osseous repair constituted 60% of the reparative process.

AREAS OF UTILITY

The results of applicant's evaluation indicate that copolymer-decalcified freeze-dried bone implant material was very successful at stimulating bone repair and that it can be used as an unexpectedly superior alternative to the agents commonly employed for bone repair and reconstruction. In addition to these areas of utility, the novel copolymer-decalcified freeze-dried bone material could be useful for bone fixation and augmentation; in liquid form to cover eroded dental enamel, cementum or dentin, or used to reinforce brittle fingernails or toenails.

In light of the present technique of osseous grafting with its inherent complications, this material may reduce the morbidity associated with the surgical repair, replacement, and augmentation of bone. Since grafts are usually employed in a particulate form, they are sometimes difficult to retain in the surgical site. The proposed invention is employed in a solid block and would eliminate this problem. The rigidity of this material may allow its use as a fixation device in discontinuity-type bony defects. This material, while being biodegradable, does not require a second surgical procedure for its procurement, or its removal. In addition to autogenous bone, this material would be the only available osteoinductive agent for bone repair.

This material would eliminate the necessity of performing a second surgical procedure on the same patient to obtain a material suitable for grafting. The material would be suitable for use in any patient (it is not patient specific as a graft or transplant would be). Unlike presently used off-the-shelf type materials such as hydroxyapatite (Calcitite TM), durapatite, (Periograft TM), and tricalcium phosphate (Synthograft TM) which are all osteoconductive, this material may be osteoinductive (similar to autogenous bone grafts). The material may be fashioned in a mold to any geometrical shape desired.

The copolymer-decalcified freeze-dried bone material has applications in orthopedics or dentistry where a bone substitute material is desired. Specifically, it may be used for:

(1) nonunions of bone;
(2) augmentation of bone;
(3) repair of bony wounds, especially discontinuity defects whidh would not be expected to heal by physiologic means; and
(4) repair of bony defects caused by:
   (a) trauma (automobile and industrial accidents and gunshot wounds),
   (b) ablation of tumors,
   (c) developmental deformities.

I claim:

1. A method for promoting the healing of osseous tissue which comprises implanting at the site of the broken osseous tissue a therapeutically-effective amount of a composition comprising decalcified freeze-dried bone incorporated into a biodegradable polymeric matrix comprised of a copolymer of poly(L)(−)lactide co-glycolide.

2. The method of claim 1 wherein said bone is cortical bone which was decalcified in 0.6 normal hydrochloric acid.

3. The method of claim 1 wherein the amount of the decalcified freeze-dried bone is about 40 to 60 percent by weight of said polymeric matrix.

4. The method of claim 3 wherein the amount of the decalcified freeze-dried bone is about 45 to 55 percent by weight of said polymeric matrix.

5. The method of claim 4 wherein the amount of decalcified freeze-dried bone is about 50 percent of said polymeric matrix.

6. The method of claim 1 wherein the copolymer is 50:50 poly(L)(−)lactide co-glycolide.

7. The method of claim 6 wherein the amount of decalcified freeze-dried bone is about 50 percent of said copolymer.

8. The method of claim 7 wherein the decalcified freeze-dried bone has a particle size in the range of 149 to 590 $\mu$m.

9. The method of claim 8 wherein the decalcified freeze-dried bone has a particle size in the range of 200 to 400 $\mu$m.

10. The method of claim 2 wherein the amount of decalcified freeze-dried bone, having a particle size in the range of 200 to 400 $\mu$m, is about 50 percent by weight and the copolymer is 50:50 poly(L)(−)lactide co-glycolide.

11. A pharmaceutical composition useful in promoting the healing of broken osseous tissue comprising decalcified freeze-dried bone incorporated into a biodegradable polymeric matrix comprised of a copolymer of poly(L)(−)lactide co-glycolide.

12. The composition of claim 11 wherein said bone is cortical bone which was decalcified in 0.6 normal hydrochloric acid.

13. The composition of claim 12 wherein the amount of decalcified freeze-dried bone is about 40 to 60 percent by weight of said polymeric matrix.

14. The composition of claim 13 wherein the amount of decalcified freeze-dried bone is about 45 to 55 percent by weight of said polymeric matrix.

15. The composition of claim 14 wherein the amount of decalcified freeze-dried bone is about 50 percent by weight of said polymeric matrix.

16. The composition of claim 15 wherein the copolymer is 50:50 poly(L)(−)lactide co-glycolide.

17. The composition of claim 16 wherein the decalcified freeze-dried bone has a particle size in the range of 149 to 590 $\mu$m.

18. The composition of claim 16 wherein the decalcified freeze-dried bone has a particle size in the range of 200 to 400 $\mu$m.

19. The composition of claim 18 wherein said bone is cortical bone which was decalcified in 0.6 normal hydrochloric acid, and incorporated into said copolymer in the amount of 50 percent by weight.

* * * * *

UNITED STATES PATENT AND TRADEMARK OFFICE
CERTIFICATE OF CORRECTION

PATENT NO. : 4,637,931

DATED : January 20, 1987

INVENTOR(S) : John P. Schmitz

It is certified that error appears in the above-identified patent and that said Letters Patent is hereby corrected as shown below:

On page 1, first line of the title, "POLYACTIC" should be --POLYLACTIC--.

Column 1, line 2, "POLYACTIC" should be --POLYLACTIC--.

Column 5, line 4, after the word "use", insert the parenthesis symbol "(".

Column 5, line 48, "Tekmoor" should be --Tekmar--.

Column 7, line 6, "whidh" should be --which--.

Signed and Sealed this

Twenty-sixth Day of January, 1988

*Attest:*

DONALD J. QUIGG

*Attesting Officer*     *Commissioner of Patents and Trademarks*